United States Patent
Allen et al.

(10) Patent No.: US 6,342,242 B1
(45) Date of Patent: Jan. 29, 2002

(54) SEAWEED SUPPLEMENT DIET FOR ENHANCING IMMUNE RESPONSE IN MAMMALS AND POULTRY

(75) Inventors: Vivien Gore Allen, Lubbock; Kevin R. Pond, Wolfforth, both of TX (US); Korinn E. Saker; Joseph P. Fontenot, both of Blacksburg, VA (US)

(73) Assignees: Texas Tech University, Lubbock, TX (US); Virginia Tech Intellectual Properties, Inc., Blacksburg, VA (US)

( * ) Notice: Subject to any disclaimer, the term of this patent is extended or adjusted under 35 U.S.C. 154(b) by 0 days.

(21) Appl. No.: 09/032,104

(22) Filed: Feb. 27, 1998

(51) Int. Cl.$^7$ ............................ A61K 47/00; A61L 9/04; A23L 1/05

(52) U.S. Cl. ........................ 424/439; 424/44; 426/575; 514/885

(58) Field of Search ................... 424/439, 44; 426/575; 514/885

(56) References Cited

U.S. PATENT DOCUMENTS 5,229,118 A  7/1993 Campbell ................. 424/195.1
5,843,762 A * 12/1998 Moll ........................ 435/257.1

FOREIGN PATENT DOCUMENTS

JP    54-40176    3/1979

OTHER PUBLICATIONS

Matzuzaki, Application of seaweeds to human nutrition and medicine, CA (AN 97:4974), 1997.*

Hershkoviz et al, Differential effects of polysulfated polysaccharide on experimental encephalomyelitis, proliferation of autoimmune Tcells . . . BIOSIS AN 1996:22174), 1996.*

Kim et al, The Effect of Dietary Sargassum–Natans and Ascophyllum Nodosum on Salmonella–Gallinarum Infection In Chicks. Biosis (AN1969:8848), 1969.*

Nishizawa, K., Seaweed as food for controlling diseases in elderly patients, CAPLUS (AN 1998:590009).

Kim, C. S., The Effects of Dietary Sargassum–Natans and Ascophyllum–Nodosum on Salmonella–Gallinarum Infection in Chicks, BIOSIS (AN 1973:82740).

Charreau, B., et al., Efficiency of fucans in protecting porcine endothelial cells against complement activation and lysis by human serum, BIOSIS (AN 1997:190627).

Blondin, C., et al., Relationships between chemical characteristics and anticomplementary activity of fucans, BIOSYS (AN 1996:188236).

Ren, D., et al., Study on Antihypertensive and Antihyperlipidemic Effects of Marine Algae, BIOSIS (AN 1994:487915).

Klinger, M. M., et al., Anti–HIV Activity of Sulfated Polysaccharides from the Brown Seaweed Ascophyllum nodosum, DRUGU M (AN 91–25081).

Blunden, G., et al., Medicinal and Pharmaceutical Uses of Algae, DRUGU TMPS (AN 87–01915).

Brochure titled Field Trial Summaries, Impact of Acadian Seaplants Seaweed Extract on Agricultural Crops, Acadian Seaplants Limited, Nova Scotia, Canada (undated).

(List continued on next page.)

Primary Examiner—Edward J. Webman

(57) ABSTRACT

Seaweed harvested from the ocean when ground as an intact meal or exposed to alkaline hydrolsis extraction procedure resulting in a water soluble form provides a feed ingredient with mineral composition and plant growth regulating activity when included as a pasture treatment or feed ingredient for mammals and poultry, resulting in enhanced immune function, enhanced health, weight gain, and meat grade quality. Steers grazing seaweed extract treated forage continued to exhibit enhanced immune function after entering feedlot phase finishin with no seaweed extract diet supplement.

14 Claims, 8 Drawing Sheets

OTHER PUBLICATIONS

Product and Technical Information, Ascophylluns nodosum Kelp Meal and Flour, Acadian Seaplants Limited, Nova Scotia, Canada (Jan. 10, 1998).

Information Sheet on Acadian Seaplants Seaweed Extract, Acadian Seaplants Limited, Nova Scotia, Canada, Jan. 8, 1998.

Brochure titled Acadian Seaplants Seaweed Extract Soluble Powder or Liquid, Acadian Seaplants Limited, Nova Scotia, Canada (undated).

Information Sheet titled Product and Technical Information, General Home and Garden Use, Acadian Seaplants Limited, Nova Scotia, Canada (Sep. 5, 1998).

Brochure titled Acadian on Grapes, Grower's Success Series, Acadian Seaplants Limited, Nova Scotia, Canada (undated).

Brochure titled Acadian Seaplants Kelp Meal (100% Ascophyllum nodosum) For Soil Applications, Acadian Seaplants Limited, Nova Scotia, Canada (undated).

Fike, J. H., et al., Proc. 1997 Amer. Forage and Grassl. Counc., Georgetown, TX, 6:153–157.

Schmidt, R. E., et al., Proc. 1997 Amer. Forage and Grassl. Counc., Georgetown, TX, 6:158–162.

Coelho, R. W., et al., Proc. 1997 Amer. Forage and Grassl. Counc., Georgetown, TX, 6:163–167.

Allen, V. G., et al., Proc. 1997 Amer. Forage and Grassl. Counc., Counc., Georgetown, TX, 6:168–172.

Saker, K. E., et al., Proc. 1997 Amer. Forage and Grassl. Counc., Georgetown, TX 6:178–182.

Okai, Y., et al., J. Sci. Food Agric. 72, 455–460 (1966).

Okai, Y., et al., J. Sci. Food Agric. 76, 56–62 (1998).

Woodard, L., Vistas, Texas Tech Research, Fall, 1999, vol. 8, No. 1, pp. 20–25.

Saker, K. E., et al., J. Anim. Sci. 76, 2694–2700 (1998).

Derwent Abstract of BE 626884 (Jan. 1963).

Hobbs, D., The New Farm May/Jun. 1994, 26–28.

Klober, K., Small Farm Today, Aug. 1996, p. 10.

Hobbs, D., "The Quest for a Water Soluble Mineral" (undated).

Hobbs, D., "Kelp Cures Copper" (undated).

Morrison, F. B., Fields and Feeding, The Morrison Publishing Company, Ithaca, NY (1957), p. 554.

Dennis, S. B., et al., J. Anim. Sci. 76, 2687–2693 (1998).

Fike, J. H., Masters Thesis titled Influence of Seaweed Extract and Other Plant Growth Regulators on Growth,. Persistence and Quality of Tall Fescue and Their Potential to Alleviate Tall Fescue Toxicity to Livestock (1995).

Hobbs, D., "Benefit of Foliar Applied Seaweed Extract" (undated).

Sen, T. L., Seaweed and Plant Growth (1987), pp. 7–4, 7–5.

Buttery, S., Influence of Acremonium Coenophialum on Fescue Arundinacea Growth, Chemical Composition, Digestibility and Tall Fescue Toxcities; Ph.D. dissertation, 1989, abstract and pp. 36, 84AND 86.

* cited by examiner

SEAWEED SUPPLEMENT DIET FOR ENHANCING IMMUNE RESPONSE IN MAMMALS AND POULTRY

BACKGROUND OF THE INVENTION

1. Field of the Invention

The invention relates to seaweed and treated seaweed feed supplements for mammals and poultry wherein the host exhibits enhanced immune response. In another aspect, the invention relates to the introduction of seaweed supplement directly to mammal and poultry feed as well as introduction of grazing animals to plants and grasses, which have been pre-treated with seaweed extract. In still another aspect, the invention relates to seaweed feed supplement, which enhances the host immune system for periods beyond cessation of seaweed supplement introduction to the host diet.

2. Description of Related Art

Seaweeds have been used through antiquity in crop production and as early as the 1950's, evidence of plant growth hormones in seaweed was reported. Seaweed is now recognized as a source of plant growth regulators and has been demonstrated to have activity that includes cytokinin, auxin, gibberellin, and idole acidic acid. Seaweed has also long served as feed for domestic and wild animals. Some even graze on seaweed growing on rocky beaches and floating in the ocean water. Seaweeds have been dried and sold as a meal product to be mixed with other feed stuffs. The value of seaweed has been generally attributed to the fact that it is low in carbohydrate and proteins and rich in trace elements; including B,D,E and other vitamin precursors including beta-carotene; and various growth hormones. Previous seaweed products are not always uniformly effective because of various contents of the trace elements and vitamins in other compounds due to the time and location of harvest and the method of processing. Therefore, seaweed products have not always provided significant reliable benefit to the host being fed the product.

Bacterial, fungal, viral and other disease causing agents inflict mammals including man, other mammals, plants, insects and poultry. The prevention and control of, for example, diseases have important health and economic implications. Diseases contribute to infections in humans and other mammals including common colds, herpes and cancer and the importance of their control is obvious. Also important is control of agent diseases in mammals and poultry for economic reasons as well as the ability of such mammals and poultry to become disease reservoirs or carriers, which facilitates the spreading of diseases to other host including humans. Plant diseases have been known to have a disruptive effect on the cultivation of fruit trees, tobacco and various vegetables as well as the utilization of plant leaves and grasses by grazing animals.

The prevention and control of diseases is thus of prime importance to man, other mammals and poultry; considerable research has been devoted to anti-disease measures. Prior research efforts have described water soluble extracts from marine red algae selected from the group consisting of *Turnerella mertensiana, Schizymenia epiphytic, Turnerella pennyi* and mixtures thereof as effective to inhabit the growth of herpes simplex virus, Type 1 and Type 2 and herpes zoster and to relieve the pain caused by infection attributable to such viruses.

Applications of materials containing high concentration of hormones reduced plant stress and enhance plant tolerance to drought and salinity. Seaweed, an excellent source of cytokinins and auxins has been associated with enhanced root development of grasses grown under stress environments. Concentrations of antioxidants increase significantly in response to exogenous seaweed treatments. Increase of these antioxidants had been correlated with photosynthetic capacity of plants subject to environmental stress. Advantages utilizing seaweed products have been defined as increasing the "livability" of animals including livestock and poultry fed the seaweed supplement along with various other additives. When animals, mammals and poultry are grown for food production, there is generally a loss of a small but constant percentage of the animals prior to bringing the animals to the market which may be due to lack of nutrients, sickness, improper growing temperature and the like. This means that the feed eaten prior death of the animals and other costs expended on the animals, which do not survive, are wasted. In addition, animals consuming costly feed for fattening which have lowered immune systems also waste the cost of the feed and decreases the weight gains of poultry and mammals and thus their economic value.

It has now been found that seaweed materials, both meal and water-soluble extract forms of seaweed enhance immune responses in mammals and poultry when introduced into the host diet either directly or indirectly through plants including forages.

SUMMARY OF THE INVENTION

Seaweed feed supplements have been found to enhance immune response in mammals. Various seaweed plant classifications have been utilized in agriculture and include such plant orders as: (1) Laminariaceae; (2) Fucaceae; and (3) Gigartinaceae. *Ascophyllum nodosum* is the most widely used form of seaweed utilized in agriculture and belongs to the order Fucaceae. Other important genus groups include Laminaria, Durvillea, Macrocystis, Chondrus, and Ecklonia.

*Ascophyllum nodosum*, the most researched seaweed for agricultural purposes is found growing in the littoral zone, that is, the coastline between high and low tides, of the North Atlantic Ocean extending from Nova Scotia to Norway. In accordance with the present invention, seaweed meal and an extract of seaweed, which is water soluble, derived by alkaline hydrolsis extraction procedures, are utilized with positive results. Seaweed meal that is dried, ground as well as extract seaweed has been utilized in accordance with the invention. Both products are commercially available, stable, with a sustainable quality assurance supply available.

The invention as directed to use of seaweed, for example, *Ascophyllum nodosum* to improve immune response in mammals and poultry. The seaweed is harvested from the ocean and ground as an intact meal which can be exposed to alkaline hydrolsis extraction procedures providing a water soluble feed ingredient with known mineral composition and plant growth regulating activity. When the seaweed is included as a pasture treatment or feed ingredient for ruminant and non-ruminant animals, poultry, and other mammals, the immune function is enhanced and health of the host is improved. Studies show sheep that grazed treated forage had increased blood levels of vitamin A and selenium indicating that the anti-oxidant activity had been increased in the host as well as in plants that the mammals grazed. In addition, influence of the seaweed extract on steers that grazed forage infected with an endophyte fungus, known to result in several animal disorders, provided further evidence that the steers had improvement in their immune function. Steers that grazed the fungus infected forage had depressed immune function that treatment with seaweed was able to reverse and to restore normal levels. Further, the improved immune function acheived by the cattle grazing on the aforementioned pasture was retained through feedlot finishing even without continuation of the seaweed supplement being furnished to the diet. Weaned pigs were fed different rates of seaweed extract or seaweed meal. These pigs were stressed by exposure to disease present within the swineherd at the time of the experiment. The seaweed extract and meal were effective in improving the health of the pigs resulting in increased growth rates, feed intake and feed efficiency. No pigs fed the extract or meal died while three deaths occured within the control group.

Improvement in immune function for mammals and poultry has large implications in the field of mammal and poultry health. Improvement in immune function in swine may well indicate applications to human health and immune function as well. Improved carcass characteristics were shown by cattle, which grazed on forage treated with seaweed extract. The monetary benefits to the industry will be significantly impacted in the positive from producing foraging animals wherein the forage has been treated by seaweed extract. Furthermore, the seaweed treatment of fescue, for example, infected with the fungus can at least offset the negative effects of immune function and will improve animal performance during the final finishing periods i.e. feedlots. Since fescue is a major pasture grass in much of the livestock producing areas of the eastern U.S., the implications are far reaching.

The invention was also productive in providing grazing lambs improved antioxidant function, daily gains and total gains as compared to control lambs grazing non-treated pastures.

Other aspects or features of the invention will be more fully apparent from the following disclosure and appended claims.

DETAILED DESCRIPTION OF THE INVENTION

Seaweed studies involved various greenhouses and small plot fields trials in order to examine the effects of seaweed extract on growth of endophyte infected and non-infected tall fescue (*Festuca arundinacea*). Thirty-two weather lambs grazed infected tall fescue that was treated with 0, 1.7, and 3.4 kg per hectare (ha) of seaweed extract. An additional treatment applied 19 L of VTMix/ha. VTMix was a combination of seaweed extract plus several other ingredients including added iron. There were four replications of each treatment and two lambs per paddock for a total of eight lambs per treatment. Lambs were grazed during two periods: May 21–June 17 (26 days) and July 19–August 10 (21 days). During the first grazing period, there was little effect of treatments on any of the measurements that were made.

Figure 1:
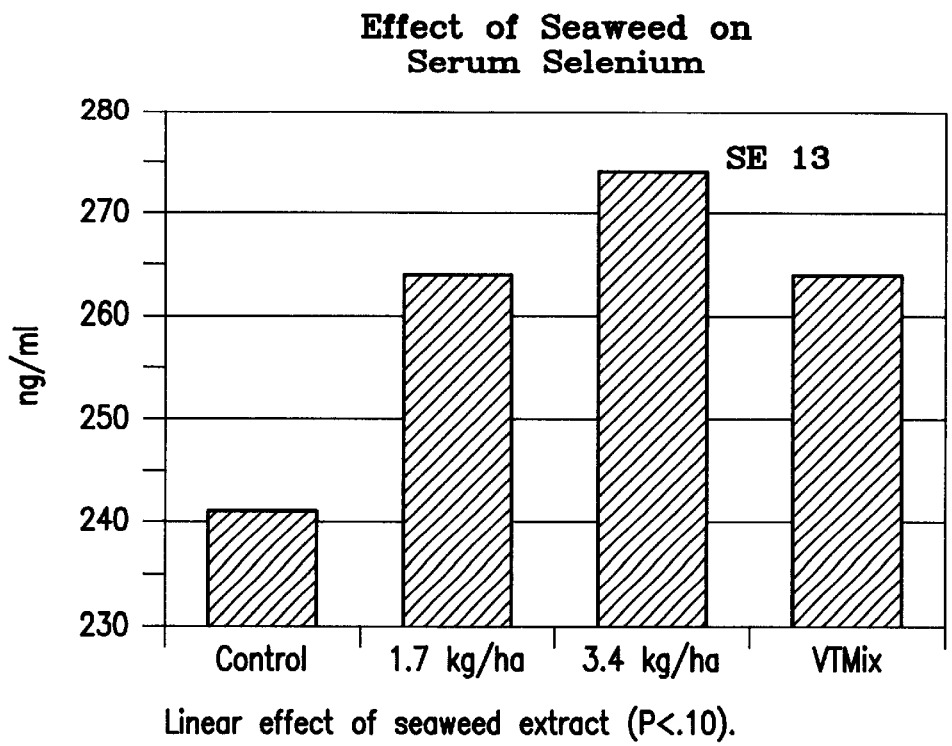
FIG. 1 is a graphic presentation of the effect of seaweed on lamb serum selenium inclusive of control and VTMix.
Figure 2:
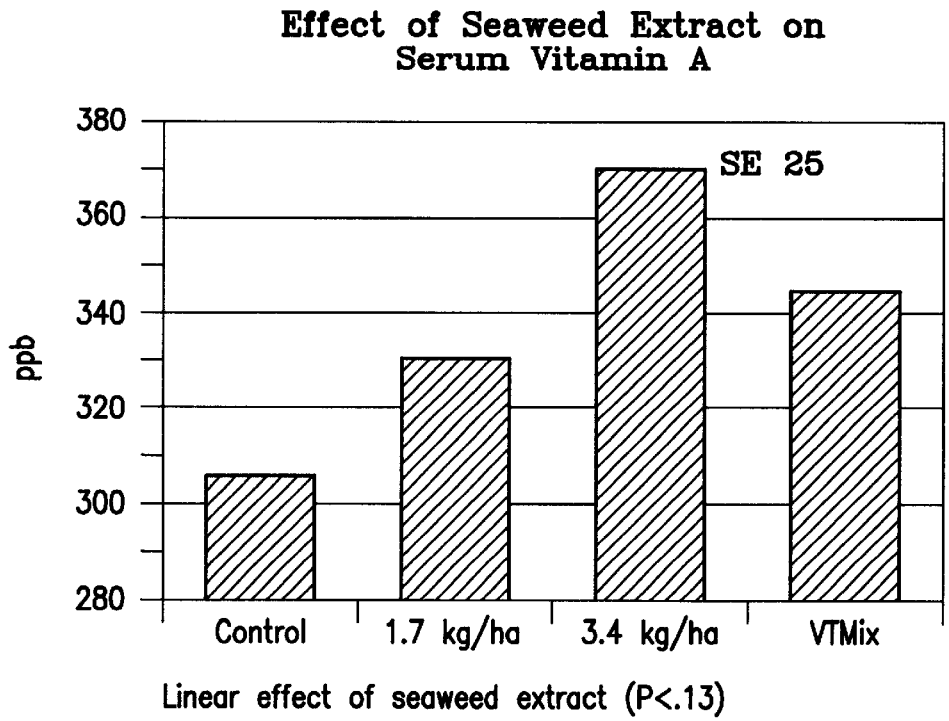
FIG. 2 is a graphic presentation of the effect of seaweed on lamb serum Vitamin A inclusive of control and VTMix.
Figure 3A:
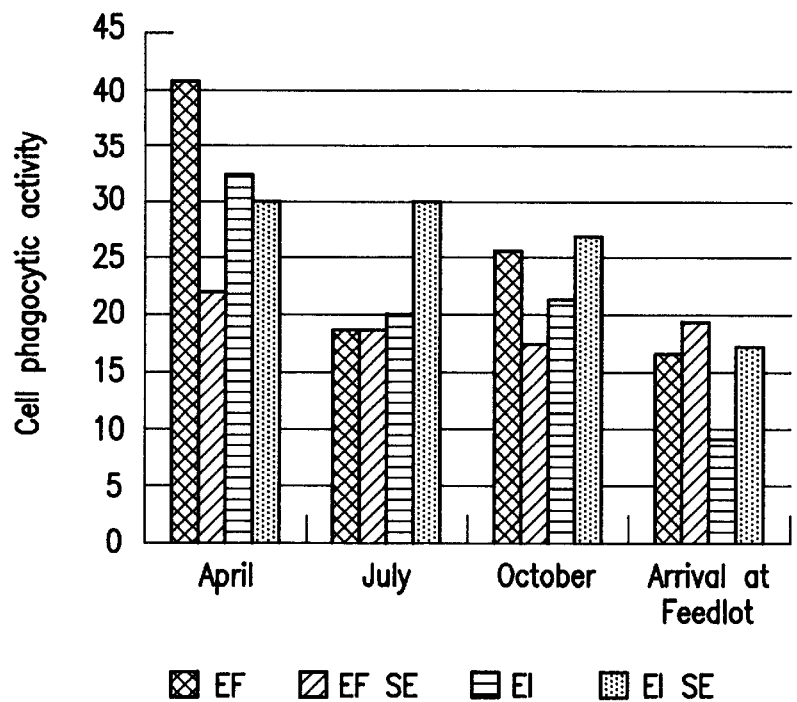
FIG. 3a is a graphic presentation of the effect of seaweed extract and endophyte infection on immune cell response of steers grazing tall fescue.
Figure 3B:
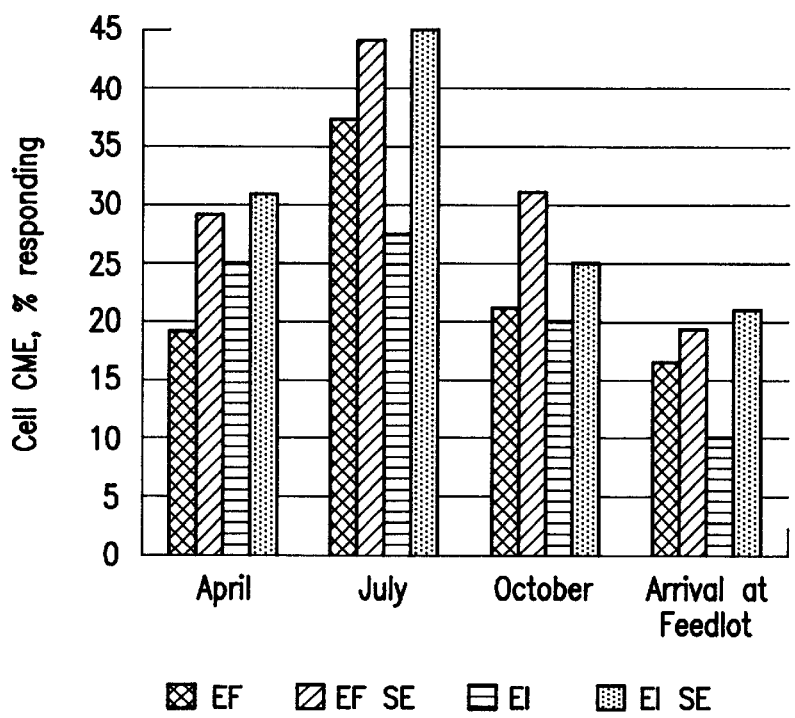
FIG. 3b is a graphic presentation of the effect of seaweed extract and immune function as measured by cell surace marker expression (CME) of steers grazing tall fescue.

During the second grazing period, average daily gains and total gains of lambs grazing the treated pastures were higher than lambs grazing the control non-treated pastures. There was a linear increase in gain with the increasing rates of seaweed applied. Application of seaweed in the VTMix did not give any added improvement over the seaweed alone. Serum selenium increased linearly with increased seaweed application. An increase in selenium likely indicated an increase in glutathione peroxidase in the animal. Serum vitamin A increased linearly in response to seaweed application. Serum vitamin A in the lambs grazing the VTMix treated pastures was intermediate to the values observed for low and high seaweed rates. (FIGS. 1 and 2)

The thirty-two wether lambs (Dorset×Rambouillet×Finn) grazed endophyte-infected (70%) tall fescue during two experimental periods (26 and 21 days). Lambs were blocked by weight, randomized within blocks, and assigned to one of three treatments in a complete randomized block design with four replications/treatment (Statistical Analysis Syste: SAS, 1985). Treatments, applied foliarly on April 5 and May 20, were 0, 1.5, and 3.0 lb SWE acre. Paddocks were 0.09 acre in size. Lambs had access to water and NaCl blocks at all times. Lambs were weighed and blood was collected by jugular puncture at the beginning and end of each trial period. Lambs were weighed and re-randomized to treatments 4 day prior to Period 2.

Samples to determine forage mass and nutritive value were taken prior to initiation of each period and 31 days after the end of Period 2. Forage mass samples also were taken at the end of each period. All paddocks were mowed at the end of the Period 1 to equilibrate forage mass per paddock. Samples were analyzed for concentrations of neutral detergent fiber (NDF), acid detergent fiber (ADF), hemicellulose, cellulose, lignin (Goering and VanSoest, 1970), crude protein (CP; A.O.A.C., 1980), and total nonstructural carbohydrate (TNC; David, 1976; Smith, 1981). In vitro dry matter digestibility (IVDMD; Tilly and Terry, 1963; Barnes, 1969) also was determined on the samples. Forage was also analyzed for pyrollizidine (University of Kentucky, Lexington, Ky.) and ergot (Auburn Fescue Diagnostic Laboratory, Auburn, Ala.) alkaloids. For Period 2, serum was analyzed for vitamins A and E, and whole blood was analyzed for Se (VAMD College of Veterinary Medicine). Plant and serum minerals were determined by inductively coupled plasma spectrometry.

Although there was no effect of treatment during Period 1, lambs grazing forage treated at the high SWE rate maintained weight while control lambs lost weight (Table 1). Lambs grazing treated forage had greater ADG in Period 2 than did wethers on control pastures. No effect of treatment was seen on serum vitamin E concentrations, but serum vitamin A increased linearly. Selenium in whole blood (measured after Period 2 only) was increased by SWE treatment.

TABLE 1

Influence of seaweed extract (SWE) on average daily gain, serum vitamin A, serum Zn, and whole blood Se of wether lambs grazing endophyte-infected tall fescue.

| | SWE. lb/acre | | | |
|---|---|---|---|---|
| Item | 0 | 1.5 | 3.0 | S.E. |
| Period 1 | | | | |
| Average daily gain, lb/d | −.07 | −.11 | 0 | .07 |
| Period 2 | | | | |
| Average daily gain, lb/d[a] | .07 | .26 | .24 | .07 |
| Serum vitamin A, ppb[b] | 306 | 331 | 371 | 25 |
| Whole blood Se, ppb[c] | 241 | 264 | 274 | 13 |

[a]Indicates difference between control vs the mean of SWE treatments (P ≤ .05).
[b]Linear effect of SWE (P ≤ .13).
[c]Linear effect of SWE (P ≤ .10).

Seaweed treatment of infected tall fescue increased antioxidant activity in the animal, a first step toward the potential to alter immune function and animal health.

Livestock grazing tall fescue infected with an endophtye [*Neotiphodium coenophialum* (Morgan Jones and Gams) Glenn, Bacon, and Hanlin] exhibit several disorders collectively refereed to as "Fescue Toxicity" (Steudemann and Hoveland, 1988). The endophyte may influence mineral composition of the plant and mineral metabolism in the animal (Buttrey, 1989). Cattle grazing E+ tall fescue exhibited signs of Cu deficiency (Coffey et al., 1991; Saker et al., 1997. Selenium and vitamin E have been investigated in relation to fescue toxicity although results have been inconsistent. Fike et al. (1997) reported that lambs grazing E+ tall fescue treated with seaweed extract showed increased whole blood Se and serum vitamin A. Thus, the relationships of endophyte and seaweed extract on performance and mineral status of steers were investigated.

Tall fescue is one of the most important forages grown and it is used widely because it is highly productive and resistant to a number of stresses. Most tall fescue is infected with a fungus, which lives inside the plant. The plant provides a home to the fungus, and the fungus helps the plant to tolerate stresses such as drought and insects. However, animals which graze-infected fescue often had low weight gain, reduced milk production, lowered conception rates and other health problems. The possibility was reviewed that the quality of tall fescue could be improved and its toxicity reduced by use of plant growth regulators. Seaweed extract is known to contain plant growth regulating compounds, and it was applied to tall fescue. Lambs grazing seaweed extract forage had greater weight gains and also had increased concentrations of vitamin A and selenium in their blood. The results show that it is possible to improve the production of animals grazing tall fescue and that seaweed extract will be helpful in reducing tall fescue toxicity.

Forty-eight yearling Angus and Angus X Hereford steers were randomized to four paddocks of E+ (80%) and four paddocks of E− (<5%) Ky-31' tall fescue at Glade Spring, Va. in 1995 and 1996. Forty-eight yearling ¾ Angus×¼ Brahman steers were randomized to four paddocks of E+ (100%) and four paddocks of E− (<5%) Ky-31 tall fescue at Prairie, MS in 1996. At each location, two paddocks of E+ and two paddocks of E− tall fescue were sprayed with seaweed extract (*A. nodosum;* Acadian Seaplants Limited, Dartmouth, Nova Scotia, Canada) at 3 lb/acre before steers began grazing in April and again in mid-summer. At both locations, steers grazed continuously from April until October. Steers were weighed and rectal temperatures were recorded initially, every 28 days, and at the end of the grazing season. All cattle received standard health care including immunizations for *Pasteurella hemoletica,* Infections Bovine rhinotrachetis, Bovine Virus Diarrhea, Clostridia perfringes C&D and were treated with Ivomec for internal parasites. Blood samples were taken by jugular vena puncture initially, and in May, July, and September for analysis of serum minerals and vitamin A. Pastures were sampled each time cattle were weighed for forage mass by clipping two 20-ft strips/paddock, and samples for mineral analysis were taken by diagonally walking each paddock and sampling fescue every 20 ft.

Concentrations of minerals were determined in fescue and in blood serum by measuring atomic emission with an inductively coupled plasma spectrometer after digestion with nitric and perchloric acids. Green leaves of tall fescue were collected from within each pasture in Virginia at 28-d intervals beginning in April and ending in November for determination of SOD activity (Giannopolitis and Ries. 1977). In Mississippi, green leaves were collected from each pasture in July, September and October. These samples were frozen in liquid nitrogen in the field and were stored in a freezer at 100 degrees Fahrenheit until SOD activity was measured. Samples collected in Mississippi were transported to Virginia in liquid nitrogen and were analyzed as described previously. Phagocytic activity and cell surface marker expression (CME) of the monocyte cell population was measured using a cell-bound fluorochrome detected through flow cytometry. Data were analyzed using an ANOVA (SAS, 1985).

Figure 4:
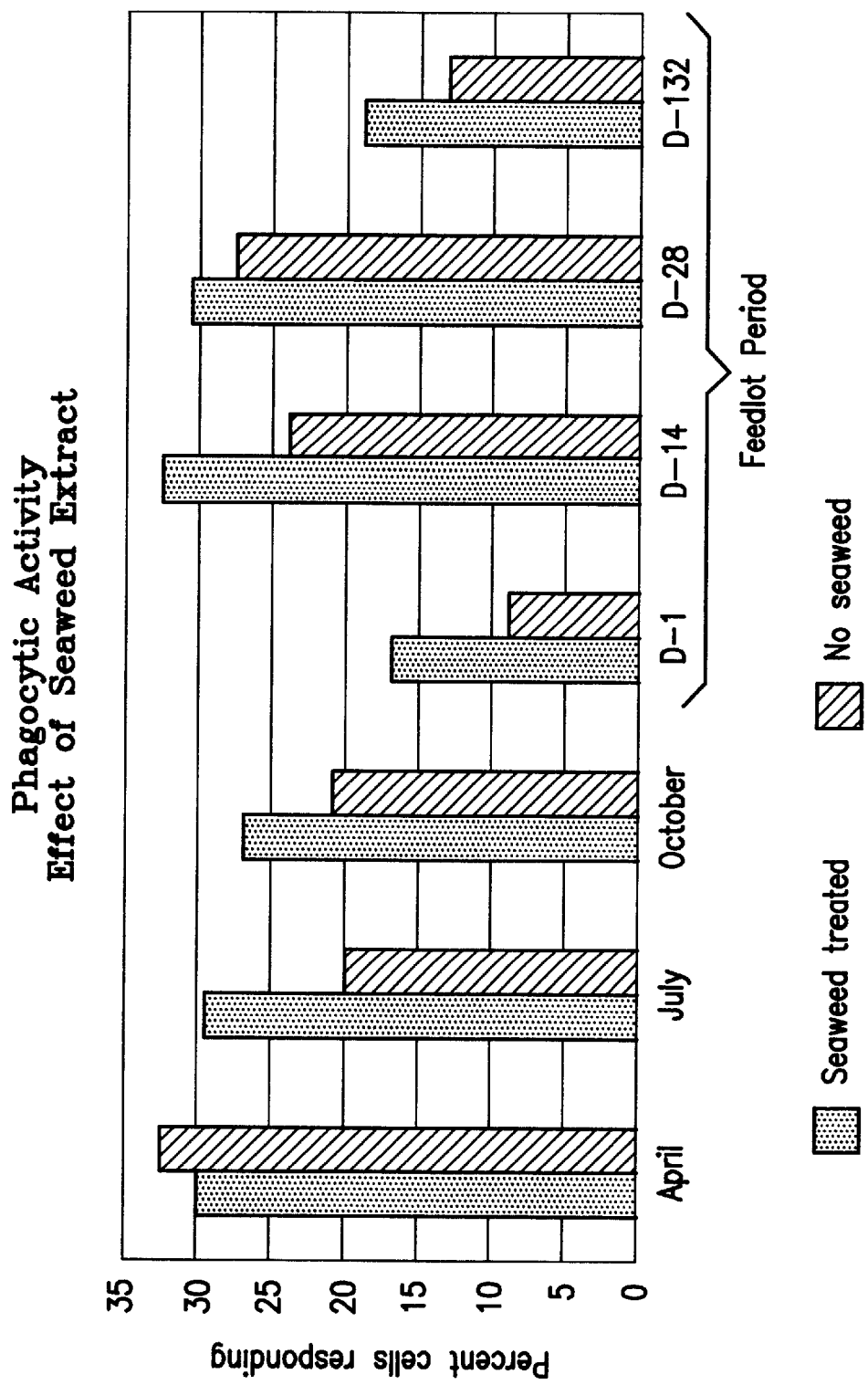
FIG. 4 is a graphic presentation of the effect of seaweed extract on phagocytic activity of steers that had grazed the treated grass prior to the feedlot period.
Figure 5:
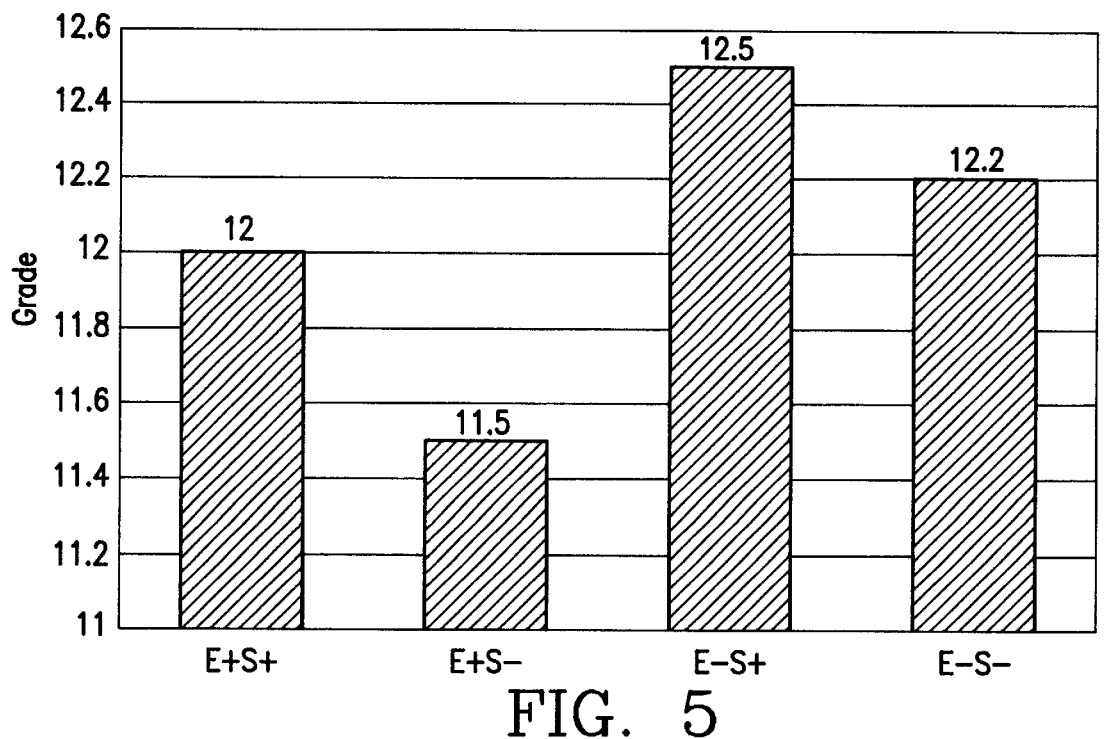
FIG. 5 is a graphic presentation of USDA Grades after feedlot phase resulting from seaweed extract treated grass grazed by steers.
Figure 6:
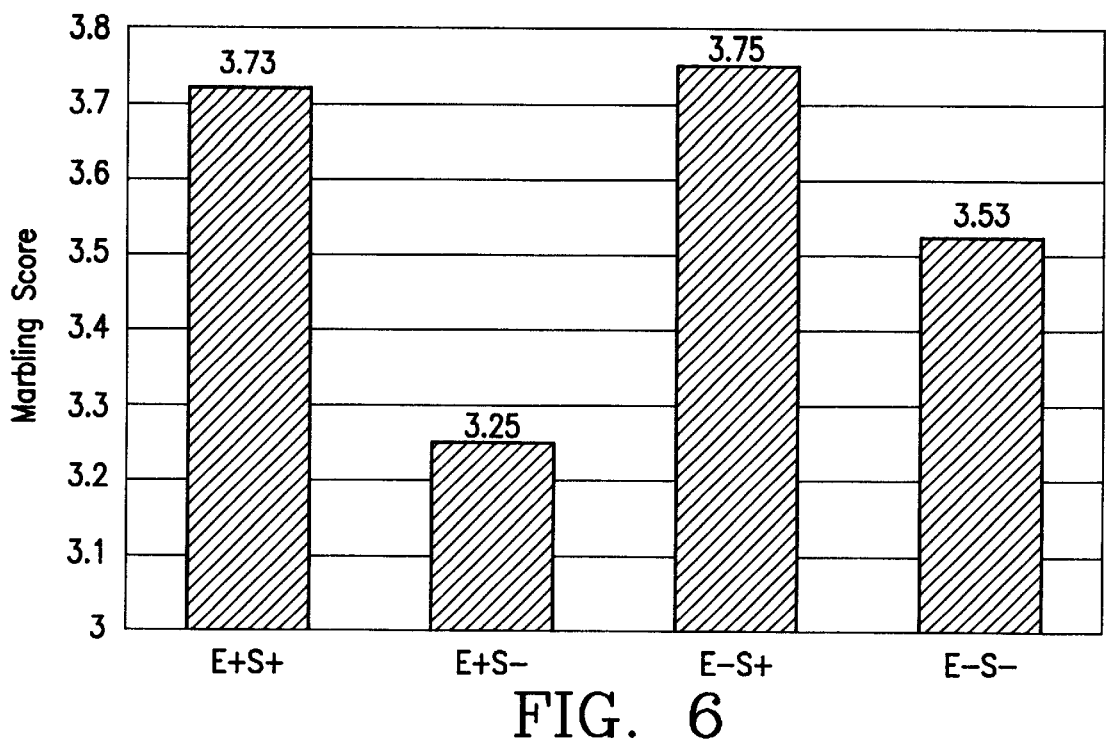
FIG. 6 is a graphic presentation of marbling score after feedlot phase resulting from seaweed extract treated grass grazed by steers.

Immune response was influenced by treatments. Total leukocyte counts were increased in Virginia steers grazed on EI-SE fescue compared to EI fescue, and this was particularly evident in July and August. However, the EF group of steers demonstrated the highest leukocyte counts of all treatment groups. Cell function appeared to be influenced by SE treatment. In 1995, an interaction of endophyte and SE treatment was observed for monocyte phagocytic activity in July only, and endophyte status influenced CME in April, June, and July. During 1996, the endophyte-seaweed extract interaction was again observed for monocyte phagocytic activity in Virginia steers. Seaweed treatment influenced CME of monocytes from steers in July, October, and at arrival to the feedlot. In general, application of SE to EI fescue enhanced immune response in grazing steers and in both EI and Ef groups during cross-country transport to the feedlot (FIG. 4). Antioxidant activity of SE, particularly SOD, a Cu-dependent enzyme, may have influenced the immunocompetence of these steers directly by increasing steer SOD concentrations or indirectly as a source of bioavailable copper in the diet to enhance monocyte function.

Immune function responses were similar to those observed during the earlier Virginia trials. Increase immune function in cattle that grazed seaweed treated pastures (both infected and non-infected fescue) remained with cattle during transportation to the feedlot and throughout the 132 day finishing period. Carcass evaluation showed that cattle that had grazed the seaweed treated pastures had USDA carcass grades that were about ½ a grade higher than cattle not exposed to seaweed. Furthermore, an increase in marbling of the meat was indicated. (FIGS. 3,4,5 and 6)

These trials provided further evidence that a positive immune response resulted from treatment of forage with seaweed and that it was not restricted to the endophyte infected fescue. These trials also provided evidence that the response was long term (132 days) after treatment ended and that there was an improvement in carcass value related to seaweed treatment.

Direct Feeding Trials

Two groups of steers (48 cattle in each group) were fed 0, 1.5, or 3% by weight of their total daily dry matter intake as seaweed meal. Group one steers were fed a diet based on sorghum while group two was fed a diet based on corn. The trial was continued for 129 days at which time all steers were slaughtered.

Figure 7:
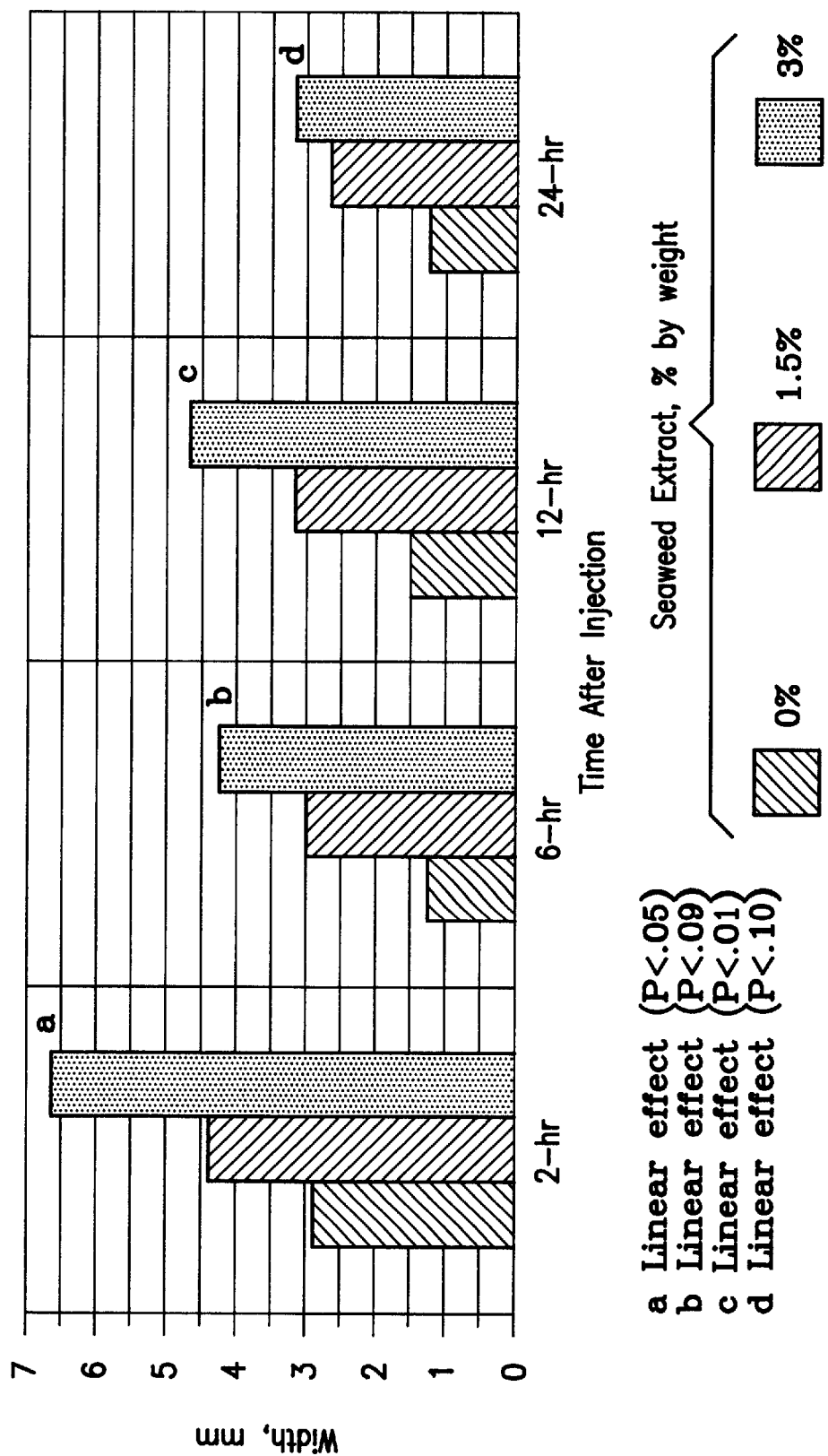
FIG. 7 is a graphic presentation of steer performance on seaweed meal-dry matter diet having increased immune function in regard to reaction to intradermal injections of phyto hemoaglutin.

Inclusion of seaweed meal reduced daily dry matter intake and performance of steers. However, there was increased immune function particularly in regard to reaction to intra-dermal injections of phyto hemoaglutin (FIG. 7).

Inclusion of seaweed meal directly in the diet of beef cattle resulted in enhanced immune response in some indicators but was less effective than treating pastures with seaweed extract and allowing cattle to graze the treated forage.

Direct feeding of seaweed extract to steers

Figure 8:
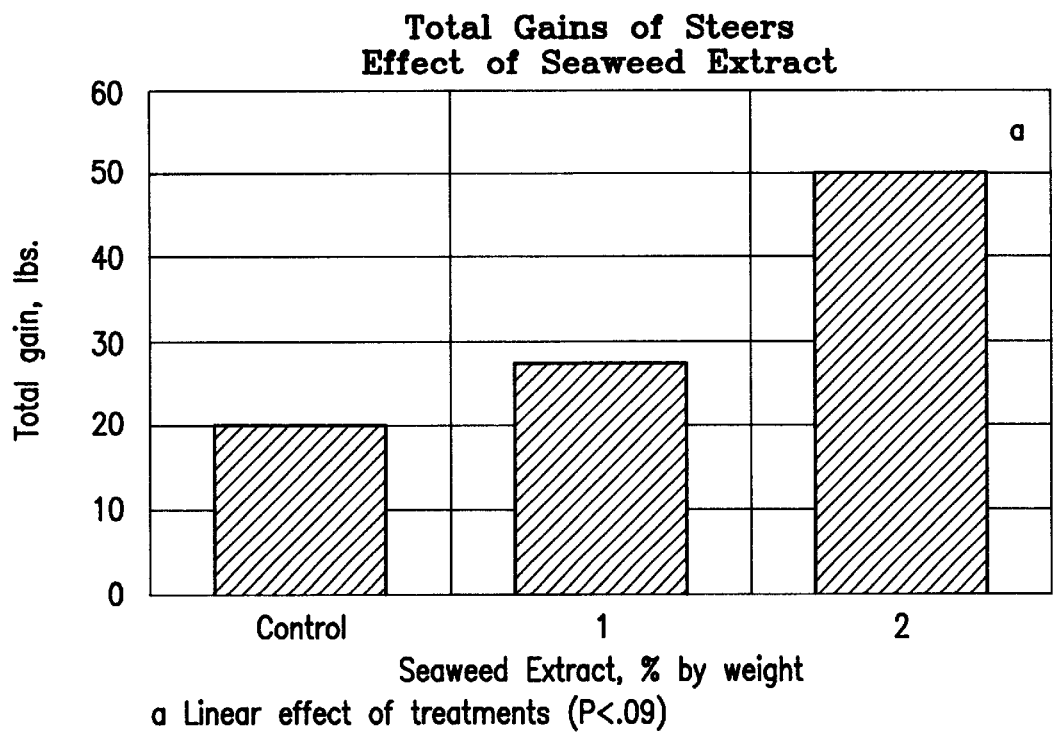
FIG. 8 is a graphic presentation of total gains of steers exposed to seaweed extract supplement during a 10 day feeding trial with seaweed extract (1and 2%) and control, followed by feedlot finishing.
Figure 9:
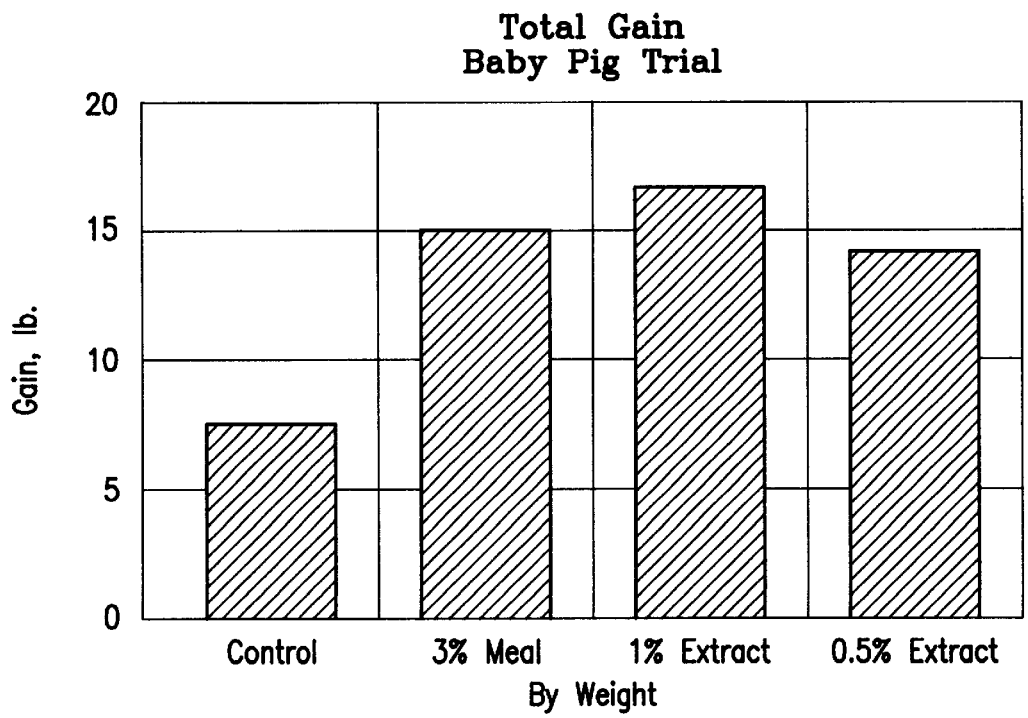
FIG. 9 is a graphic presentation of baby pig trial total gain for control, seaweed meal, 1% seaweed extract; 0.5% seaweed extract.
Figure 10:
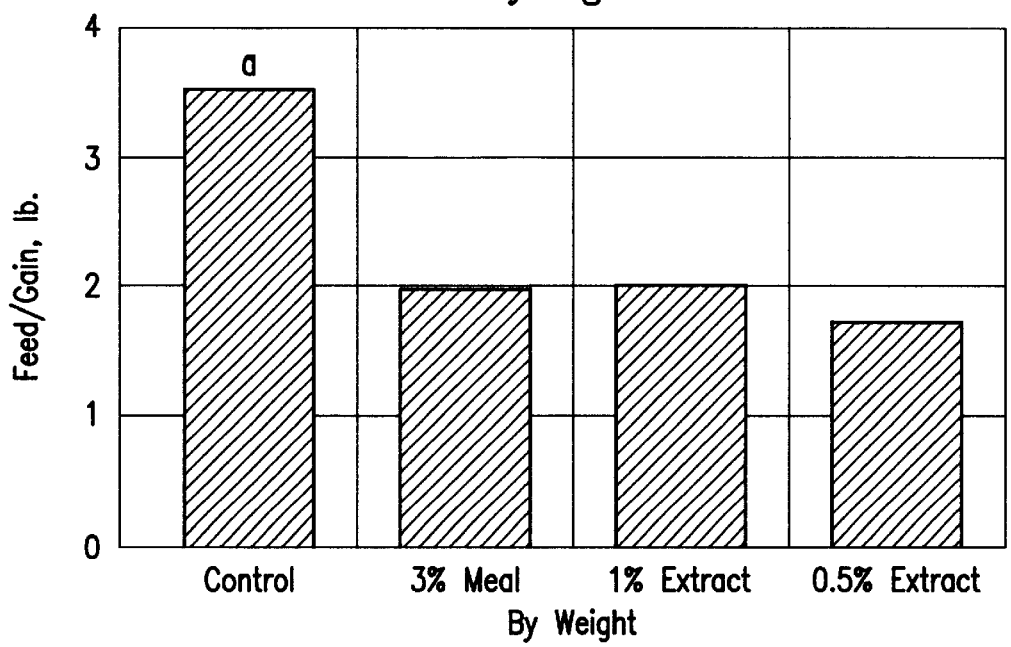
FIG. 10 is a graphic presentation of baby pig trial feed to gain for control, seaweed meal, 1% seaweed extract; 0.5% seaweed extract.
Figure 11:
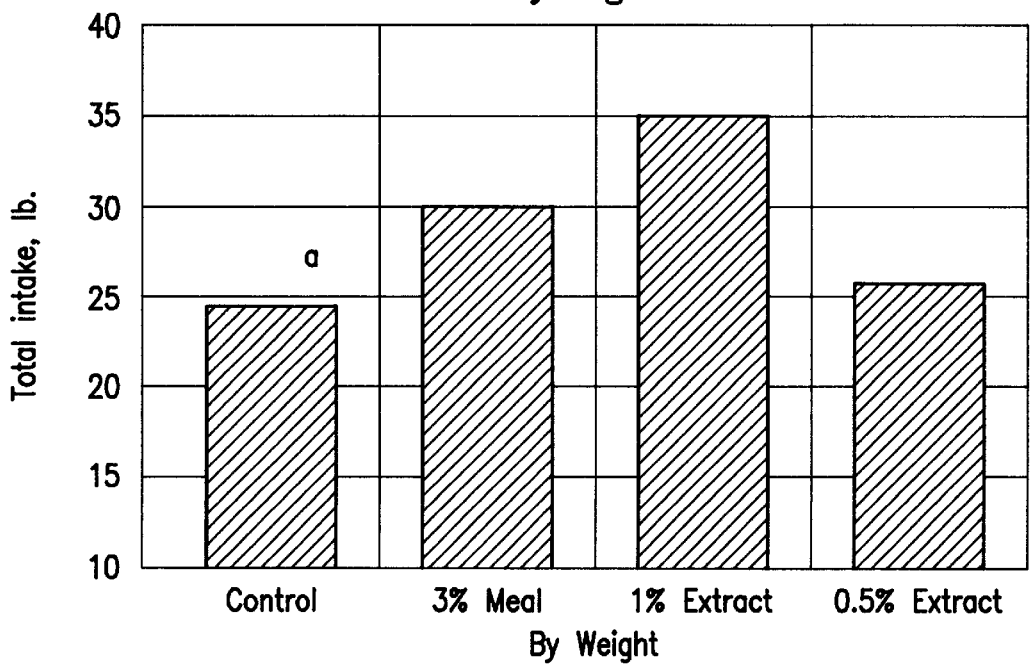
FIG. 11 is a graphic presentation of baby pig trial total intake per pig for control, seaweed meal, 1% seaweed extract; 0.5% seaweed extract.
Figure 12:
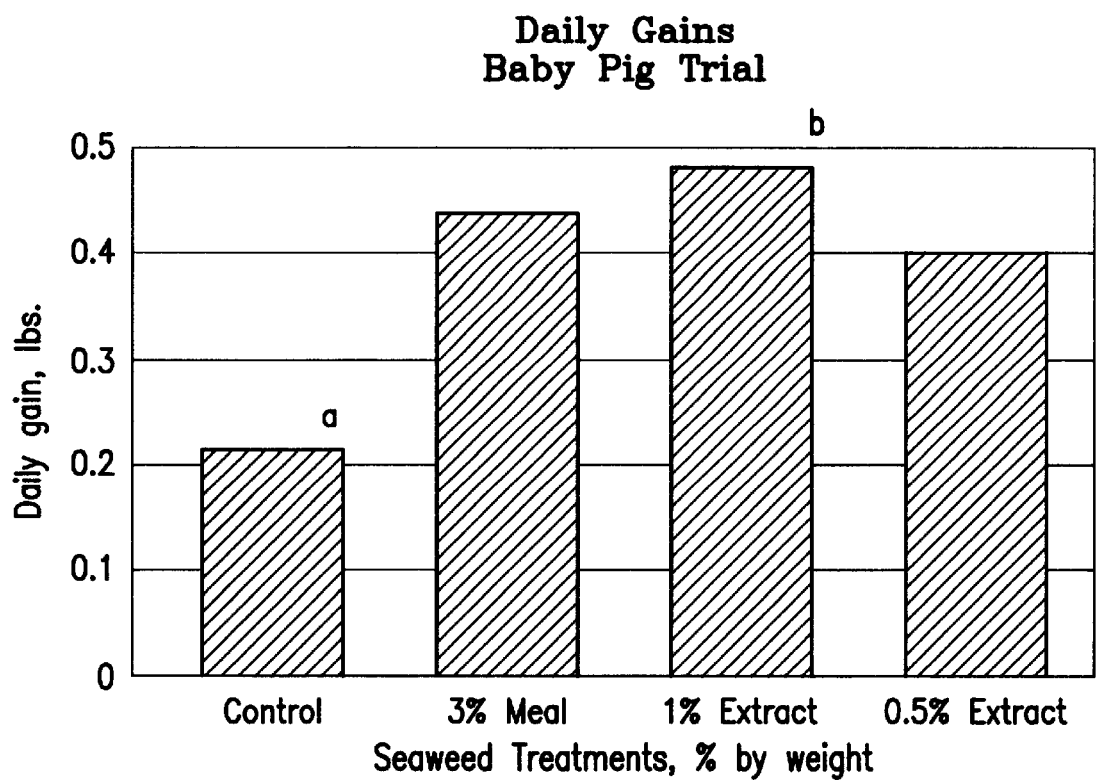
FIG. 12 is a graphic presentation of baby pig trial daily gains for control, seaweed meal, 1% seaweed extract; 0.5% seaweed extract.

Twenty-four steers were fed a diet of 0,1, and 2% seaweed extract for 10 days in a feeding trial. At the end of the 10-day period, the extract was removed from the diet and all steers were fed the control diet. Daily gains are being recorded. The results indicated a trend for a linear increase in total and daily gain in response to seaweed level (FIG. 8). The improvement in performance appears to be consistent with the previous research with pigs and lambs.

Direct feeding of seaweed extract and seaweed meal to swine.

One hundred and eight baby pigs were fed the following diets. Control, 1% seaweed meal, and 1% seaweed extract as a percentage of daily dry matter intake. There were four pens (replications) per treatment with eight pigs per pen. Additionally one treatment group was fed the 1% seaweed meal for 8 days and was then returned to the control diet for the duration of the trial. Pigs were started on the experimental diets a few days after weaning and were fed the diets during a 35-day period. Weights of pigs and feed intake were determined weekly. All pigs had been exposed to Porcine Respiratory and Reproductive Syndrome. Additionally, these pigs had been exposed to a skin staphylococcus infection.

Results: Pigs fed the 1% extract for only 8 days appeared to have feed intake and daily gains similar to controls but had reduced incidence of the staphylococcus infection. Feeding the extract or meal during the entire study period did not increase the tolerance to the staff infection.

Implications: Short term dosing may provide the improvement in disease tolerance without the lowered feed intake observed in previous trials.

One hundred and twenty-eight baby pigs were blocked by weight and breed and were randomized within blocks to four treatments as follows: Control, 3% seaweed meal, 0.5% seaweed extract, and 1% seaweed extract as a percentage by weight of the diet. There were four pens (replications) per treatment with eight pigs per pen. Pigs were started on the experimental diets at weaning and were fed the diets during a 35-day period. Weights of pigs and feed intake were determined weekly. All pigs had been exposed to Porcine Respiratory and Reproductive Syndrome.

Pigs fed the seaweed-enhanced diets gained more total weight and had improved feed efficiency compared to control pigs (FIGS. 9,10,11 and 12). Performance of control pigs declined over the feeding period while performance of treated pigs improved. Direct feeding of seaweed as meal or extract improved feed efficiency and animal performance during disease challenge indicating an increased tolerance to disease.

For purposes of this specification and figures the following abbreviations are defined as follows;

| | |
|---|---|
| S.E. | standard error; |
| E.F. | endophyte free; |
| E.F.S.E. | endophyte free plus seaweed; |
| E.I. | endophyte infected; |
| E.I.S.B. | endophyte infected plus seaweed; |
| E+ | endophyte infected; |
| E− | no endophyte infection; |
| S+ | with seaweed; and |
| S− | without seaweed. |

The terms and expressions which have been employed are used as terms of description and not of limitation, and it is not intended in the use of such terms and expressions to exclude an equivalence of the features shown and described or portions thereof, since it is recognized that various modifications are possible within the scope of the invention claimed.

What is claimed is:

1. A method of enhancing immune response as manifested by increased cell surface marker expression of monocytic cell population, in mammals in need of this enhanced immune response, comprising: introducing seaweed extract which is water soluble and which is obtained by a method comprising alkaline hydrolysis extraction of seaweed, to the diet of the mammals in amounts of from 0.10% to about 3.0% by weight of diet or greater for a period of from about three to about seven days or longer.

2. The method according to claim 1 wherein the seaweed is introduced into the diet for a period of from about 5 to 14 days or longer.

3. The method according to claim 1 wherein the mammals are selected from the group consisting of man, cattle, swine and sheep.

4. The method according to claim 1 wherein the seaweed is selected from the plant orders group consisting of Aminariaceae, Fucaceae, Gigartinoceae, Alaminaria, Durrillea, Macrocystis, Chondrus, Ecklonia and Ascophyllum.

5. The method according to claim 4 where the seaweed is *Ascophyllum nodosum* and is selected from the plant order Fucaceae.

6. A method for enhancing immune response as manifested by increased cell surface marker expression of monocytic cell population in forage consuming mammals in need of this enhanced immune response, comprising: introducing seaweed extract which is water soluble and which is obtained by a method comprising alkaline hydrolysis extraction of seaweed onto the forage in amount of from about 0.10 to about 4.0 kg per hectare or greater; and grazing the mammals on the forage treated with the seaweed extract for a period of about seven days or longer.

7. The method according to claim 6 wherein the forage consuming mammals are sheep.

8. The method according to claim 6 wherein the forage consuming mammals are horses.

9. The method according to claim 6 wherein the forage consuming mammals are goats.

10. The method according to claim 6 wherein the forage consuming mammals are swine.

11. The method according to claim 6 wherein the forage consuming mammals are cattle.

12. The method of claim 6 wherein the forage is endophyte-infected forage.

13. The method of claim 12 wherein the endophyte-infected forage is endophyte-infected tall fescue.

14. The method of claim 13 wherein the forage consuming mammals are cattle and the seaweed is *Ascophyllum nodosum*.

* * * * *